United States Patent
Senn-Bilfinger et al.

(10) Patent No.: US 6,927,292 B2
(45) Date of Patent: Aug. 9, 2005

(54) TRICYCLIC EPOXIDES

(75) Inventors: Jörg Senn-Bilfinger, Constance (DE); Peter Jan Zimmermann, Radolfzell (DE)

(73) Assignee: Altana Pharma AG, Constance (DE)

( * ) Notice: Subject to any disclaimer, the term of this patent is extended or adjusted under 35 U.S.C. 154(b) by 0 days.

(21) Appl. No.: 10/485,418

(22) PCT Filed: Jul. 31, 2002

(86) PCT No.: PCT/EP02/08499

§ 371 (c)(1),
(2), (4) Date: Jan. 30, 2004

(87) PCT Pub. No.: WO03/014119

PCT Pub. Date: Feb. 20, 2003

(65) Prior Publication Data

US 2004/0176597 A1 Sep. 9, 2004

(30) Foreign Application Priority Data

Aug. 2, 2001 (EP) ............................................ 01118592
Feb. 15, 2002 (DE) ......................................... 102 06 625

(51) Int. Cl.[7] ...................... C07D 491/22; C07D 471/12

(52) U.S. Cl. .............................. 546/64; 546/65; 546/82; 546/83; 544/125

(58) Field of Search .............................. 546/64, 65, 82, 546/83; 544/125

(56) References Cited

FOREIGN PATENT DOCUMENTS

| WO | WO 98/42707 | 10/1998 |
|---|---|---|
| WO | WO 98/54188 | 12/1998 |
| WO | WO 00/17200 | 3/2000 |
| WO | WO 00/26217 | 5/2000 |
| WO | WO 00/63211 | 10/2000 |

OTHER PUBLICATIONS

"Reaktionen von Nucleosiden mit dem System Triphenyl–phosphan/Diethyl–azodicarboxylat", Mengel et al., *Angewandte Chemie* 90:9 (1978).

*Primary Examiner*—Charanjit S. Aulakh
(74) *Attorney, Agent, or Firm*—Nath & Associates PLLC; Joshua B. Goldberg; Sheldon M. McGee

(57) ABSTRACT

The invention relates to compounds of Formula (1), in which the substituents and symbols have the meanings indicated in the description. The compounds are valuable intermediates for the preparation of pharmaceutical active compounds.

10 Claims, No Drawings

TRICYCLIC EPOXIDES

TECHNICAL FIELD

The Invention relates to novel compounds which are used in the pharmaceutical industry as valuable intermediates for the preparation of active compounds.

PRIOR ART

The International patent applications WO 98/42707, WO 98/54188, WO 00/17200, WO 00/26217 and WO 00/63211 disclose tricyclic imidazopyridine derivatives having a very specific substitution pattern, which should be suitable for the treatment of gastric and intestinal disorders.—Mengel et al. descibe the synthesis and reaction of certain epoxides (Angewandte Chemie 1978, page 725).

DESCRIPTION OF THE INVENTION

The invention relates to compounds of the formula 1

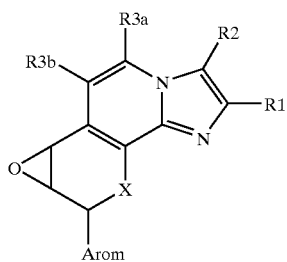

(1)

in which
R1 is hydrogen, 1–4C-alkyl, 3–7C-cycloalkyl, 3–7C-cycloalkyl-1–4C-alkyl, 1–4C-alkoxy, 1–4C-alkoxy-1–4C-alkyl, 1–4C-alkoxycarbonyl, 2–4C-alkenyl, 2–4C-alkynyl, fluoro-1–4C-alkyl or hydroxy-1–4C-alkyl,
R2 is hydrogen, 1–4C-alkyl, 3–7C-cycloalkyl, 3–7C-cycloalkyl-1–4C-alkyl, 1–4C-alkoxycarbonyl, hydroxy-1–4C-alkyl, halogen, 2–4C-alkenyl, 2–4C-alkynyl, fluoro-1–4C-alkyl or cyanomethyl,
R3a is hydrogen, halogen, fluoro-1–4C-alkyl, 1–4C-alkyl, 2–4C-alkenyl, 2–4C-alkynyl, 1–4C-alkoxy, carboxyl, 1–4C-alkoxycarbonyl, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32,
R3b is hydrogen, halogen, fluoro-1–4C-alkyl, 1–4C-alkyl, 2–4C-alkenyl, 2–4C-alkynyl, 1–4C-alkoxy, carboxyl, 1–4C-alkoxycarbonyl, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32,
where
R31 is hydrogen, 1–7C-alkyl, hydroxy-1–4C-alkyl or 1–4C-alkoxy-1–4C-alkyl and
R32 is hydrogen, 1–7C-alkyl, hydroxy-1–4C-alkyl or 1–4C-alkoxy-1–4C-alkyl,
or where
R31 and R32 together, including the nitrogen atom to which both are bonded, are a pyrrolidino radical, piperidino radical or morpholino radical,
Arom is a mono- or bicyclic aromatic radical substituted by R4, R5, R6 and R7, which is selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuryl), thiophenyl (thienyl), benzothiophenyl (benzothienyl), thiazolyl, isoxazolyl, pyridinyl, pyrimidinyl, quinolinyl and isoquinolinyl,
where
R4 is hydrogen, 1–4C-alkyl, hydroxy-1–4C-alkyl, 1–4C-alkoxy, 2–4C-alkenyloxy, 1–4C-alkylcarbonyl, carboxyl, 1–4C-alkoxycarbonyl, carboxy-1–4C-alkyl, 1–4C-alkoxycarbonyl-1–4C-alkyl, halogen, hydroxyl, aryl, aryl-1–4C-alkyl, aryloxy, aryl-1–4C-alkoxy, trifluoromethyl, nitro, amino, mono- or di-1–4C-alkylamino, 1–4C-alkylcarbonylamino, 1–4C-alkoxycarbonylamino, 1–4C-alkoxy-1–4C-alkoxycarbonylamino or sulfonyl,
R5 is hydrogen, 1–4C-alkyl, 1–4C-alkoxy, 1–4C-alkoxycarbonyl, halogen, trifluoromethyl or hydroxyl,
R6 is hydrogen, 1–4C-alkyl or halogen and
R7 is hydrogen, 1–4C-alkyl or halogen,
where
aryl is phenyl or substituted phenyl having one, two or three identical or different substituents from the group consisting of 1–4C-alkyl, 1–4C-alkoxy, carboxyl, 1–4C-alkoxycarbonyl, halogen, trifluoromethyl, nitro, trifluoromethoxy, hydroxyl and cyano,
X is O (oxygen), NH or N-Prot,
where Prot is an amino protective group,
and their salts.

1–4C-Alkyl represents straight-chain or branched alkyl radicals having 1 to 4 carbon atoms. Examples which may be mentioned are the butyl radical, isobutyl radical, sec-butyl radical, tert-butyl radical, propyl radical, isopropyl radical, ethyl radical and the methyl radical.

3–7C-Cycloalkyl represents cyclopropyl, cyclobutyl, cyclopentyl, cyclohexyl and cycloheptyl, of which cyclopropyl, cyclobutyl and cyclopentyl are preferred.

3–7C-Cycloalkyl-1–4C-alkyl represents one of the abovementioned 1–4C-alkyl radicals, which is substituted by one of the abovementioned 3–7C-cycloalkyl radicals. Examples which may be mentioned are the cyclopropylmethyl radical, the cyclohexylmethyl radical and the cyclohexylethyl radical.

1–4C-Alkoxy represents radicals which, in addition to the oxygen atom, contain a straight-chain or branched alkyl radical having 1 to 4 carbon atoms. Examples which may be mentioned are the butoxy radical, isobutoxy radical, sec-butoxy radical, tert-butoxy radical, propoxy radical, isopropoxy radical and preferably the ethoxy radical and methoxy radical.

1–4C-Alkoxy-1–4C-alkyl represents one of the abovementioned 1–4C-alkyl radicals, which is substituted by one of the abovementioned 1–4C-alkoxy radicals. Examples which may be mentioned are the methoxymethyl radical, the methoxyethyl radical and the butoxyethyl radical.

1–4C-Alkoxycarbonyl (—CO-1–4C-alkoxy) represents a carbonyl group, to which is bonded one of the abovementioned 1–4C-alkoxy radicals. Examples which may be mentioned are the methoxycarbonyl radical ($CH_3O$—$C(O)$—) and the ethoxycarbonyl radical ($CH_3CH_2O$—$C(O)$—).

2–4C-Alkenyl represents straight-chain or branched alkenyl radicals having 2 to 4 carbon atoms. Examples which may be mentioned are the 2-butenyl radical, 3-butenyl radical, 1-propenyl radical and the 2-propenyl radical (allyl radical).

2–4C-Alkynyl represents straight-chain or branched alkynyl radicals having 2 to 4 carbon atoms. Examples which may be mentioned are the 2-butynyl radical, 3-butynyl radical and preferably the 2-propynyl radical (propargyl radical).

Fluoro-1–4C-alkyl represents one of the abovementioned 1–4C-alkyl radicals, which is substituted by one or more fluorine atoms. An example which may be mentioned is the trifluoromethyl radical.

Hydroxy-1–4C-alkyl represents abovementioned 1–4C-alkyl radicals which are substituted by a hydroxyl group. Examples which may be mentioned are the hydroxymethyl radical, the 2-hydroxyethyl radical and the 3-hydroxypropyl radical.

Halogen within the meaning of the invention is bromine, chlorine and fluorine.

1–4C-Alkoxy-1–4C-alkoxy represents one of the abovementioned 1–4C-alkoxy radicals, which is substituted by a further 1–4C-alkoxy radical. Examples which may be mentioned are the radicals 2-(methoxy)ethoxy ($CH_3$—O—$CH_2$—$CH_2$—O—) and 2-(ethoxy)ethoxy ($CH_3$—$CH_2$—O—$CH_2$—O—).

1–4C-Alkoxy-1–4C-alkoxy-1–4C-alkyl represents one of the abovementioned 1–4C-alkoxy-1–4C-alkyl radicals, which is substituted by one of the abovementioned 1–4C-alkoxy radicals. An example which may be mentioned is the radical 2-(methoxy)ethoxy-methyl ($CH_3$—O—$CH_2$—$CH_2$O—$CH_2$—).

Fluoro-1–4C-alkoxy-1–4C-alkyl represents one of the abovementioned 1–4C-alkyl radicals, which is substituted by a fluoro-1–4C-alkoxy radical. Fluoro-1–4C-alkoxy here represents one of the abovementioned 1–4C-alkoxy radicals, which is entirely or mainly substituted by fluorine. Examples of 1–4C-alkoxy entirely or mainly substituted by fluorine which may be mentioned are the 1,1,1,3,3,3-hexafluoro-2-propoxy radical, the 2-trifluoromethyl-2-propoxy radical, the 1,1,1-trifluoro-2-propoxy radical, the perfluoro-tert-butoxy radical, the 2,2,3,3,4,4,4-heptafluoro-1-butoxy radical, the 4,4,4-trifluoro-1-butoxy radical, the 2,2,3,3,3-pentafluoropropoxy radical, the perfluoroethoxy radical, the 1,2,2-trifluoroethoxy radical, in particular the 1,1,2,2-tetrafluoroethoxy radical, the 2,2,2-trifluoroethoxy radical, the trifluoromethoxy radical and preferably the difluoromethoxy radical.

1–7C-Alkyl represents straight-chain or branched alkyl radicals having 1 to 7 carbon atoms. Examples which may be mentioned are the heptyl radical, isoheptyl radical (5-methylhexyl radical), hexyl radical, isohexyl radical (4-methylpentyl radical), neohexyl radical (3,3-dimethylbutyl radical), pentyl radical, isopentyl radical (3-methylbutyl radical), neopentyl radical (2,2-dimethylpropyl radical), butyl radical, isobutyl radical, sec-butyl radical, tert-butyl radical, propyl radical, isopropyl radical, ethyl radical and the methyl radical.

2–4C-Alkenyloxy represents a radical which, in addition to the oxygen atom, contains a 2–4C-alkenyl radical. An example which may be mentioned is the allyloxy radical.

1–4C-Alkylcarbonyl represents a radical which, in addition to the carbonyl group, contains one of the abovementioned 1–4C-alkyl radicals. An example which may be mentioned is the acetyl radical.

Carboxy-1–4C-alkyl represents, for example, the carboxymethyl radical (—$CH_2COOH$) or the carboxyethyl radical (—$CH_2CH_2COOH$).

1–4C-Alkoxycarbonyl-1–4C-alkyl represents one of the abovementioned 1–4C-alkyl radicals, which is substituted by one of the abovementioned 1–4C-alkoxycarbonyl radicals. An example which may be mentioned is the ethoxycarbonylmethyl radical ($CH_3CH_2OC(O)CH_2$—).

Aryl-1–4C-alkyl represents a 1–4C-alkyl radical which is substituted by aryl. An example which may be mentioned is the benzyl radical.

Aryl-1–4C-alkoxy represents a 1–4C-alkoxy radical which is substituted by aryl. An example which may be mentioned is the benzyloxy radical.

Mono- or di-1–4C-alkylamino radicals contain, in addition to the nitrogen atom, one or two of the abovementioned 1–4C-alkyl radicals. Di-1–4C-alkylamino is preferred and here, in particular, dimethyl-, diethyl- or diisopropylamino.

1–4C-Alkylcarbonylamino represents an amino group to which is bonded a 1–4C-alkylcarbonyl radical. Examples which may be mentioned are the propionylamino radical ($C_3H_7C(O)NH$—) and the acetylamino radical (acetamido radical) ($CH_3C(O)NH$—).

1–4C-Alkoxycarbonylamino represents an amino radical which is substituted by one of the abovementioned 1–4C-alkoxycarbonyl radicals. Examples which may be mentioned are the ethoxycarbonylamino radical and the methoxycarbonylamino radical.

1–4C-Alkoxy-1–4C-alkoxycarbonyl represents a carbonyl group, to which is bonded one of the abovementioned 1–4C-alkoxy-1–4C-alkoxy radicals. Examples which may be mentioned are the 2-(methoxy)ethoxycarbonyl radical ($CH_3$—O—$CH_2CH_2$—O—CO—) and the 2-(ethoxy)ethoxycarbonyl radical ($CH_3CH_2$—O—$CH_2CH_2$—O—CO—).

1–4C-Alkoxy-1–4C-alkoxycarbonylamino represents an amino radical which is substituted by one of the abovementioned 1–4C-alkoxy-1–4C-alkoxycarbonyl radicals. Examples which may be mentioned are the 2-(methoxy) ethoxycarbonylamino radical and the 2-(ethoxy) ethoxycarbonylamino radical.

The radicals Arom which may be mentioned are, for example, the following substituents: 4-acetoxy-phenyl, 4-acetamidophenyl, 2-methoxyphenyl, 3-methoxyphenyl, 4-methoxyphenyl, 3-benzyloxyphenyl, 4-benzyloxyphenyl, 3-benzyloxy-4-methoxyphenyl, 4-benzyloxy-3-methoxyphenyl, 3,5bis(trifluoro-methyl)phenyl, 4-butoxyphenyl, 2-chlorophenyl, 3-chlorophenyl, 4-chlorophenyl, 2-chloro-6-fluoro-phenyl, 3-chloro-4-fluorophenyl, 2-chloro-5-nitrophenyl, 4-chloro-3-nitrophenyl, 3-(4-chlorophenoxy)-phenyl, 2,4-dichlorophenyl, 3,4-difluorophenyl, 2,4-dihydroxyphenyl, 2,6-dimethoxyphenyl, 3,4-dimethoxy-5-hydroxyphenyl, 2,5-dimethylphenyl, 3-ethoxy-4-hydroxyphenyl, 2-fluorophenyl, 4fluoro-phenyl, 4-hydroxyphenyl, 2-hydroxy-5-nitrophenyl, 3-methoxy-2-nitrophenyl, 3-nitrophenyl, 2,3,5-trichlorophenyl, 2,4,6-trihydroxyphenyl, 2,3,4-trimethoxyphenyl, 2-hydroxy-1-naphthyl, 2-methoxy-1-naph-thyl, 4-methoxy-1-naphthyl, 1-methyl-2-pyrrolyl, 2-pyrrolyl, 3-methyl-2-pyrrolyl, 3,4dimethyl-2-pyrrolyl, 4-(2-methoxycarbonylethyl)-3-methyl-2-pyrrolyl, 5-ethoxycarbonyl-2,4-dimethyl-3-pyrrolyl, 3,4-di-bromo-5-methyl-2-pyrrolyl, 2,5-dimethyl-1-phenyl-3-pyrrolyl, 5-carboxyl-3-ethyl-4-methyl-2-pyrrolyl, 3,5-dimethyl-2-pyrrolyl, 2,5-dimethyl-1-(4-trifluoromethylphenyl)-3-pyrrolyl, 1-(2,6-dichloro-4-trifluoromethylphenyl)-2-pyrrolyl, 1-(2-nitrobenzyl)-2-pyrrolyl, 1-(2-fluorophenyl)-2-pyrrolyl, 1-(4-trifluoromethoxyphenyl)-2-pyrrolyl, 1-(2-nitrobenzyl)-2-pyrrolyl, 1-(4-ethoxycarbonyl)-2,5-dimethyl-3-pyrrolyl, 5-chloro-1,3-dimethyl-4-pyrazolyl, 5-chloro-1-methyl-3-trifluoromethyl-4-pyrazolyl, 1-(4-chlorobenzyl)-5-pyrazolyl, 1,3dimethyl-5-(4-chlorphenoxy)-4-pyrazolyl, 1-methyl-3-trifluoromethyl-5-(3-trifluoro-methylphenoxy)-4-pyrazolyl, 4-methoxycarbonyl-1-(2,6-dichlorophenyl)-5- pyrazolyl, 5-allyloxy-1-methyl-3-trifluoromethyl-4-pyrazolyl, 5-chloro-1-phenyl-3-trifluoromethyl-4-pyrazolyl, 3,5-dimethyl-1-phenyl-4-imid-azolyl, 4-bromo-1-methyl-5-imidazolyl, 2-butylimidazolyl, 1-phenyl-1,2,3-triazol-4-yl, 3-indolyl, 4-indolyl, 7-indolyl, 5-methoxy-3-indolyl, 5-benzyloxy-3-indolyl, 1-benzyl-3-indolyl, 2-(4-chlorophenyl)-3-indolyl, 7-benzyloxy-3-indolyl, 6-benzyloxy-3-indolyl, 2-methyl-5-nitro-3-indolyl, 4,5,6,7-tetrafluoro-3-indolyl, 1-(3,5-difluorobenzyl)-3-indolyl, 1-methyl-2-(4-trifluorophenoxy)-3-indolyl, 1-methyl-2-benzimidazolyl, 5-nitro-2-furyl, 5-hydroxymethyl-2-furyl, 2-furyl, 3-furyl, 5-(2-nitro-4-trifluoromethylphenyl)-2-furyl, 4-ethoxycarbonyl-5-methyl-2-furyl, 5-(2-trifluoromethoxyphenyl)-2-furyl, 5-(4-methoxy-2-nitrophenyl)-2-furyl, 4-bromo-2-furyl, 5-dimethylamino-2-furyl, 5-bromo-2-furyl, 5-sulfo-2-furyl, 2-benzofuryl, 2-thien-yl, 3-thienyl, 3-methyl-2-thienyl, 4-bromo-2-thienyl, 5-bromo-2-thienyl, 5-nitro-2-thienyl, 5-methyl-2-thienyl, 5-(4-methoxyphenyl)-2-thienyl, 4-methyl-2-thienyl, 3-phenoxy-2-thienyl, 5-carboxyl-2-thienyl, 2,5-dichloro-3-thienyl, 3-methoxy-2-thienyl, 2-benzothienyl, 3-methyl-2-benzothlenyl, 2-bromo-5-chloro-3-benzothienyl, 2-thiazolyl, 2-amino-4-chloro-5-thiazolyl, 2,4-dichloro-5-thiazolyl, 2-diethylamino-5-thi-azolyl, 3-methyl-4-nitro-5-isoxazolyl, 2-pyridyl, 3-pyridyl, 4-pyridyl, 6-methyl-2-pyridyl, 3-hydroxy-5-hydroxymethyl-2-methyl-4-pyridyl, 2,6dichloro-4-pyridyl, 3-chloro-5-trifluoromethyl-2-pyridyl, 4,6-di-methyl-2-pyridyl, 4-(4-chlorophenyl)-3-pyridyl, 2-chloro-5-methoxycarbonyl-6-methyl-4-phenyl-3-pyridyl, 2-chloro-3-pyridyl, 6-(3-trifluoromethylphenoxy)-3-pyridyl, 2-(4-chlorophenoxy)-3-pyridyl, 2,4-dimethoxy-5-pyrimidinyl, 2-quinolinyl, 3-quinolinyl, 4-quinolinyl, 2-chloro-3-quinolinyl, 2-chloro-6-methoxy-3-quinolinyl, 8-hydroxy-2-quinolinyl and 4-isoquinolinyl.

Suitable amino protective groups are in principle all protective groups, such as are used for the protection of amino acids in peptide and protein synthesis or for the protection of other amines, e.g. in alkaloid or nucleotide synthesis (for this see, for example, T. W. Greene and P. G. M. Wuts, Protective groups in organic synthesis, 2nd edition, 1991, John Wiley & Sons, Inc., pages 309–385). Protective groups which may be mentioned by way of example are the radicals 1–4C-alkylcarbonyl (e.g. acetyl), 1–4C-alkoxycarbonyl (e.g. butoxycarbonyl), benzyloxycarbonyl or nitrobenzenesulfenyl. The acetyl radical is preferred.

Suitable salts for compounds of the formula 1—depending on substitution—are especially all acid addition salts. Particular mention may be made of the salts of the customarily used inorganic and organic acids. Those which are suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in preparation of the salt—depending on whether a mono- or polybasic acid is concerned and depending on which salt is desired—in an equimolar quantitative ratio or one differing therefrom.

It is known to the person skilled in the art that the compounds according to the invention and their salts, if they are isolated, for example, in crystalline form, can contain various amounts of solvents. The invention therefore also comprises all solvates and in particular all hydrates of the compounds of the formula 1, and all solvates and in particular all hydrates of the salts of the compounds of the formula 1.

The compounds of the formula 1, in principle, have three chiral centers in the parent structure. The invention therefore relates to all conceivable stereoisomers in any desired mixing ratio with one another, including the pure enantiomers, to which the invention preferably relates.

Compounds to be emphasized are those of the formula 1, in which

R1 is hydrogen, 1–4C-alkyl, 3–7C-cycloalkyl, 1–4C-alkoxy-1–4C-alkyl, 2–4C-alkynyl or fluoro-1–4C-alkyl, R2 is hydrogen, 1–4C-alkyl, halogen, 2–4C-alkenyl, 2–4C-alkynyl or fluoro-1–4C-alkyl, R3a is hydrogen, R3b is hydrogen, halogen, 1–4C-alkyl or the radical —CO—NR31R32, where R31 is hydrogen, 1–7C-alkyl, hydroxy-1–4C-alkyl or 1–4C-alkoxy-1–4C-alkyl and R32 is hydrogen, 1–7C-alkyl, hydroxy-1–4C-alkyl or 1–4C-alkoxy-1–4C-alkyl, or where R31 and R32 together, including the nitrogen atom to which both are bonded, are a pyrrolidino radical, piperidino radical or morpholino radical, Arom is a mono- or bicyclic aromatic radical substituted by R4, R5, R6 and R7, which is selected from the group consisting of phenyl, furanyl (furyl) and thiophenyl (thienyl), where R4 is hydrogen, 1–4C-alkyl, hydroxy-1–4C-alkyl, 1–4C-alkoxy, 1–4C-alkylcarbonyl, carboxyl, 1–4C-alkoxycarbonyl, halogen, hydroxyl, trifluoromethyl, 1–4C-alkylcarbonylamino, 1–4C-alkoxycarbonylamino, 1–4C-alkoxy-1–4C-alkoxycarbonylamino or sulfonyl, R5 is hydrogen, 1–4C-alkyl, 1–4C-alkoxy, 1–4C-alkoxycarbonyl, halogen, trifluoromethyl or hydroxyl, R6 is hydrogen and R7 is hydrogen, X is O (oxygen), NH or N-Prot, where Prot is an amino protective group, and their salts.

Among the compounds according to the invention, the optically pure compounds of the formula 1*

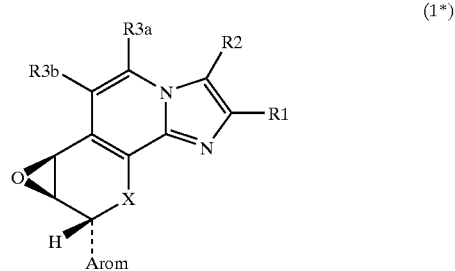

(1*)

and their salts are to be emphasized.

Particularly to be emphasized are compounds of the formula 1*, in which

R1 is hydrogen, methyl, cyclopropyl, methoxymethyl or trifluoromethyl,

R2 is hydrogen, methyl, chlorine, bromine, ethynyl or trifluoromethyl,

R3a is hydrogen,
R3b is hydrogen, fluorine, methyl or the radical —CO—N(CH₃)₂,
Arom is a phenyl radical and
X is O (oxygen), NH or N-Prot,
where Prot is an amino protective group,
and their salts.

Preferred compounds of the formula 1* are those in which
R1 is methyl,
R2 is methyl,
R3a is hydrogen,
R3b is hydrogen,
Arom is a phenyl radical and
X is O (oxygen), NH or N-Prot,
where Prot is an amino protective group,
and their salts.

The compounds of the formula 1 according to the invention, in which R1, R2, R3a, R3b and Arom have the meanings indicated above and X is O (oxygen) or N-Prot, can be prepared from the compounds of the formula 2

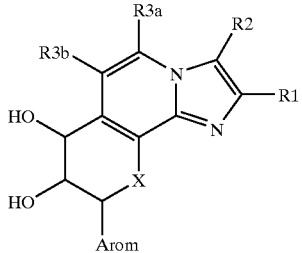

(2)

as shown by way of example in scheme 1 below for the compounds 1* and 2*:

Scheme 1:

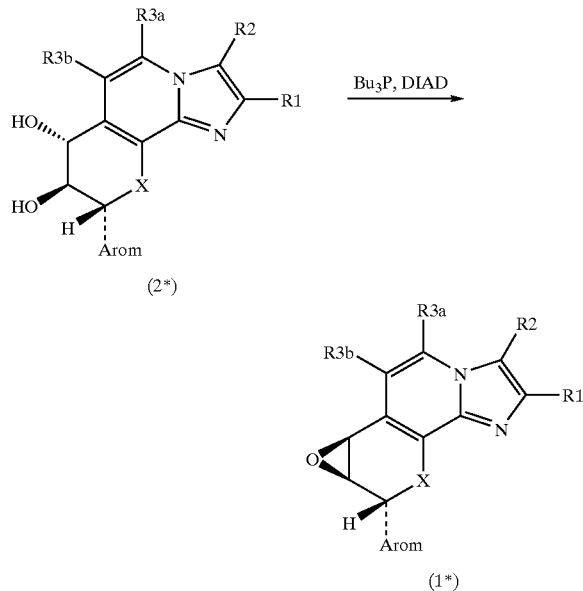

The compounds of the formula 1* or 1 in which X is NH are obtained by removal of the protective group Prot, where this removal is preferably only carried out after the further reaction according to the invention of the intermediate of the formula 1* or 1.

The compounds of the formula 1 according to the invention, in which R1, R2, R3a, R3b and Arom have the meanings indicated above and X is O (oxygen) or N-Prot, can furthermore be prepared from the compounds of the formula 3

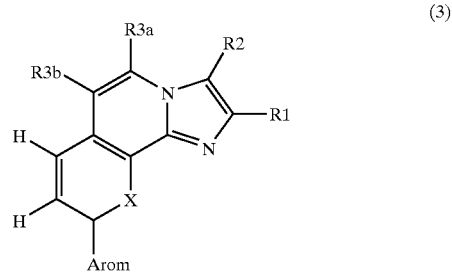

(3)

by epoxidation. Here too, the compounds of the formula 1 in which X is NH are obtained by removal of the protective group Prot, where this removal is likewise preferably only carried out after the further reaction according to the invention of the intermediate of the formula 1.

The invention further relates to the use of compounds of the formula 1, in which R1, R2, R3a, R3b and Arom have the meanings indicated above and X is O (oxygen) or N-Prot, for the preparation of compounds of the formula 4

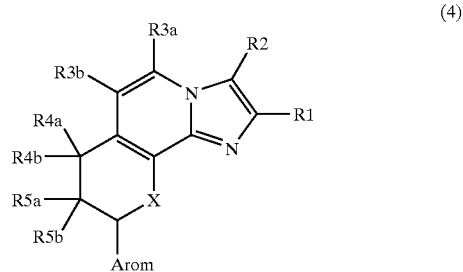

(4)

in which R1, R2, R3a, R3b, Arom and X have the meanings indicated above,
one of the substituents R4a and R4b is hydrogen and the other is 1–4C-alkoxy, 1–4C-alkoxy which is substituted by oxo, 3–7C-cycloalkoxy, 3–7C-cycloalkyl-1–4C-alkoxy, 1–4C-alkoxy-1–4C-alkoxy, 3–7C-cycloalkoxy-1–4C-alkoxy, 3–7C-cycloalkyl-1–4C-alkoxy-1–4C-alkoxy or 1–4C-alkoxy which is entirely or mainly substituted by halogen,
one of the substituents R5a and R5b is hydrogen and the other is hydroxyl,
and their salts.

The use of the compounds of the formula 1 for the preparation of the compounds of the formula 4 is carried out, for example, such that the compounds of the formula 1, in which R1, R2, R3a, R3b and Arom have the meanings indicated above and X is O (oxygen) or N-Prot, are reacted with alcohols ROH, in which RO is 1–4C-alkoxy, 1–4C-alkoxy which is substituted by oxo, 3–7C-cycloalkoxy, 3–7C-cycloalkyl-1–4C-alkoxy, 1–4C-alkoxy-1–4C-alkoxy, 3–7C-cycloalkoxy-1–4C-alkoxy, 3–7C-cycloalkyl-1–4C-alkoxy-1–4C-alkoxy or 1–4C-alkoxy which is entirely or mainly substituted by halogen, and, if desired, the amino protective group is then removed.

To be emphasized according to the invention is the use of compounds of the formula 1* for the preparation of compounds of the formula 4*,

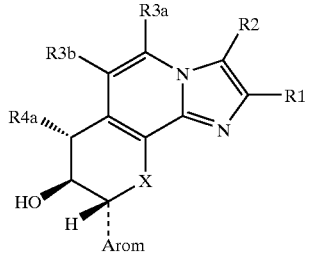

(4*)

In which R1, R2, R3a, R3b, Arom and X have the meanings indicated above,

R4a is 1–4C-alkoxy, 1–4C-alkoxy which is substituted by oxo, 3–7C-cycloalkoxy, 3–7C-cycloalkyl-1–4C-alkoxy, 1–4C-alkoxy-1–4C-alkoxy, 3–7C-cycloalkoxy-1–4C-alkoxy, 3–7C-cycloalkyl-1–4C-alkoxy-1–4C-alkoxy or 1–4C-alkoxy which is entirely or mainly substituted by halogen, and their salts.

The conversion of the diol into the epoxide according to scheme 1 is carried out in a manner known per se, e.g. using tributylphosphine and diisopropyl azodicarboxylate with cooling and under inert conditions (see, for example, J. Voss et al., Synthesis 2001, 229–234 or R. Mengel et al., Angew. Chem. 1978, 90, 725).

The compounds of the formula 2 are known or they can be prepared as described by way of example in the following examples below, or starting from appropriate starting compounds using analogous process steps (see, for example, WO 98/42707, WO 98/54188, WO 00/17200, WO 00/26217 and WO 00/63211), or as very generally outlined in the following schemes.

Scheme 2:
Preparation of compounds 2 where X = N-Prot and any desired substituents R3a and R3b (not indicated in the formulae)

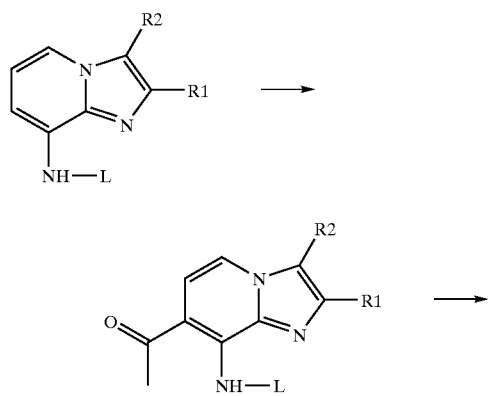

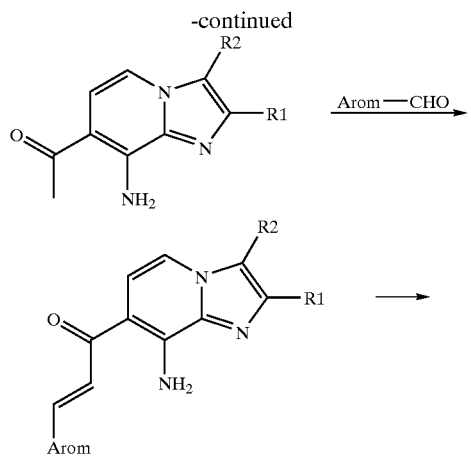

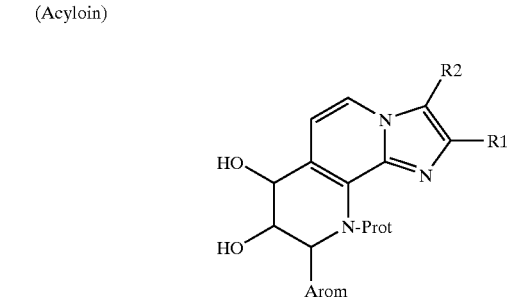

(Acyloin)

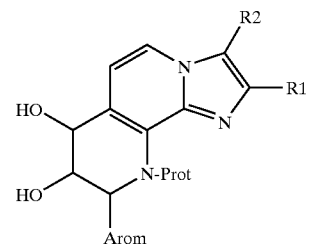

L in the above scheme represents any desired leaving group, for example a pivaloyl group. The introduction of the acetyl group and the condensation with the aldehyde Arom-CHO are carried out in a manner known per se. The epoxidation is likewise carried out in a manner known per se, for example using hydrogen peroxide as epoxidizing agent. The introduction of the O- and N-protective groups, the subsequent reduction and the following removal of the O-protective group are likewise carried out in a manner known per se, for example as described in greater detail in the following examples.

The preparation of compounds of the formula 2, shown by way of example for a compound of the formula 2*, where X=O and any desired substituents R3a and R3b, is advantageously carried out according to reaction scheme 3 below.

Scheme 3:
Preparation of compounds 2* where X = O (oxygen) and any desired substituents R3a and R3b (not indicated in the formulae)

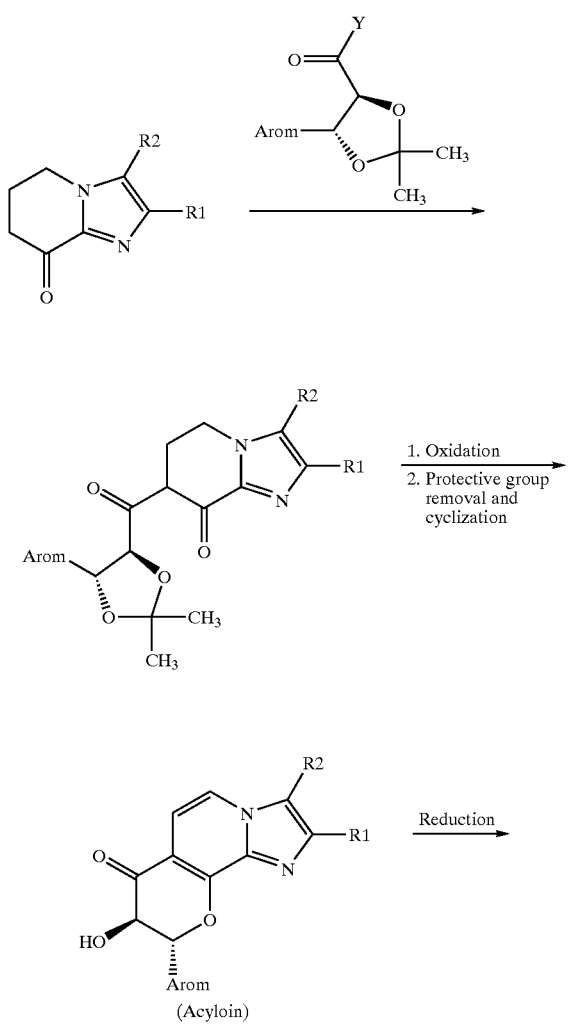

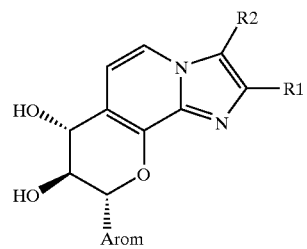

In the above scheme 3, the enantioselective synthesis of a 7,8-diol of the formula 2* where X=O (oxygen) is shown by way of example. The group Y in scheme 3 is a suitable leaving group, for example a halogen atom, preferably chlorine, or a 1–4C-alkoxy group, preferably methoxy. The acylation is carried out in a manner customary to the person skilled in the art, preferably using bis-(trimethylsilyl) sodamide or -potassamide if the leaving group is a chlorine atom.

The oxidation following the acylation is likewise carried out under conditions which are customary per se using chloroanil, atmospheric oxygen, 2,3-dichloro-5,6-dicyano-p-benzoquinone or manganese dioxide as oxidant. For the subsequent protective group removal and cyclization, certain conditions are to be fulfilled with respect to the auxiliary acid used. Preferably, formic acid is employed as an auxiliary acid.

The reduction to the diol is likewise carried out—as already in the case of the reduction according to scheme 2—under standard conditions (see, for example, WO98/54188), where, for example, sodium borohydride is employed as reductant, using which the indicated 7,8-trans-diol can be obtained in over 90% diastereomeric purity. With respect to the specific preparation and isolation of the pure enantiomers, reference is made, for example, to the appropriate details in WO00/17200. The starting compounds shown in schemes 2 and 3 are known (see, for example, EP-A-299470, Kaminski et al., J. Med. Chem. 1985, 28, 876–892, 1989, 32, 1686–1700 and 1991, 34, 533–541 and Angew. Chem. 1996, 108, 589–591) or they can be prepared analogously to the known compounds, for example according to reaction scheme 4 below.

Scheme 4:
Preparation by way of example of starting compounds needed according to scheme 3 where R1, R2 = methyl and various substituents R3b.

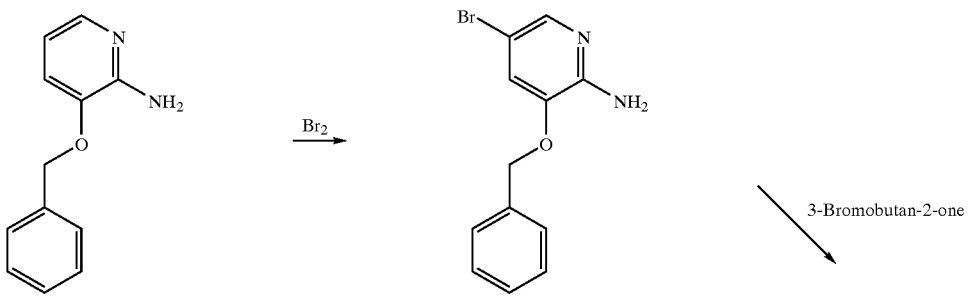

-continued

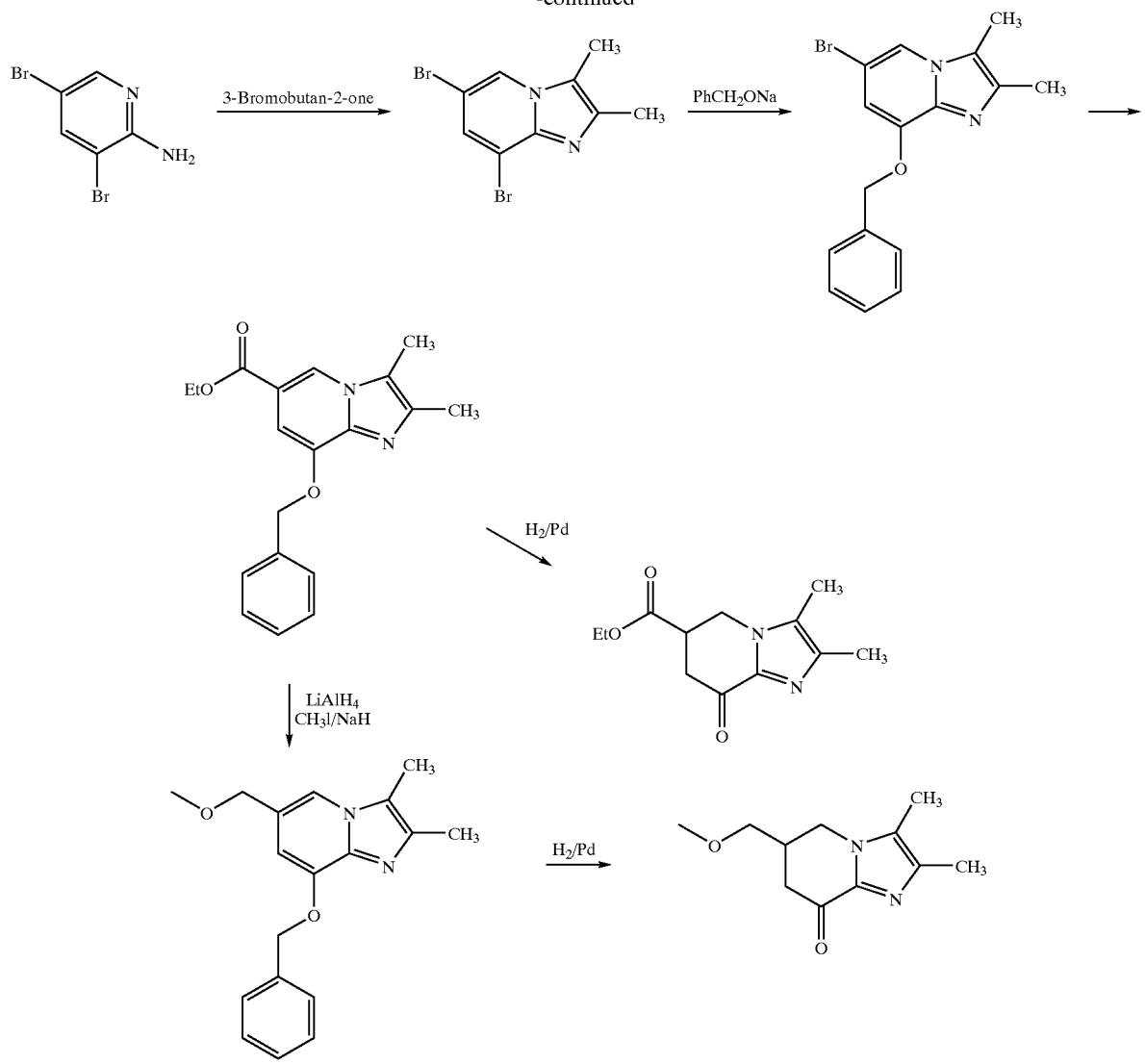

The reactions to give the 8-benzyloxy-6-bromoimidazopyridines are carried out in a manner such as is known to the person skilled in the art. The conversion of the bromine atom into an ethyl ester radical can be carried out in various ways, for example using the Heck reaction (with Pd(II), carbon monoxide and ethanol) or by metalation in the 6-position (with lithium or magnesium) and subsequent Grignard reaction. The metalation also offers the possibility of introducing other desired groups R3b into position 6, for example fluorine, chlorine or the carboxyl group. Starting from the ester group, further desired groups R3b can be introduced into position 6, for example hydroxy-1–4C-alkyl radicals (in particular the hydroxymethyl radical), by reduction of the ester radical using lithium aluminum hydride, or 1–4C-alkoxy-1–4C-alkyl radicals (in particular 1–4C-alkoxymethyl radicals) by subsequent etherification as outlined in scheme 4.

The debenzylation/reduction is likewise carried out in a manner known per se, for example using hydrogen/Pd(0). If compounds where R3b=—CO—NR31R32 are desired, an appropriate derivatization in a manner known per se (conversion of an ester into an amide) can be carried out at the stage of the 8-benzyloxy-6-ethoxycarbonyl compound or after the debenzylation/reduction, or alternatively also at a later point in time, e.g. at the stage of the acyloin (see schemes 2 and 3).

Starting compounds having various substituents R1 and R2 are known, or they can be prepared—for example on the basis of scheme 4—in a known manner in analogy to known compounds. Alternatively, derivatizations can also be carried out at the stage of the compounds 2. Thus, for example, starting from compounds where R2=H, it is possible to prepare compounds where R2=CH$_2$OH (by Vilsmeier reaction and subsequent reduction), where R2=Cl or Br (by chlorination or bromination), where R2=propynyl (from the corresponding bromo compound using the Sonogashira reaction) or where R2=alkoxycarbonyl (from the corresponding bromo compound by Heck carbonylation).

The epoxidation of the compounds of the formula 3 can be carried out with the aid of customary epoxidizing agents, preferably using hydrogen peroxide.

The compounds of the formula 3 can be prepared from the compounds of the formula 5,

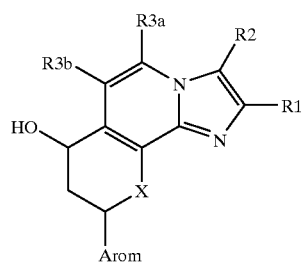

(5)

in which R1, R2, R3a, R3b and Arom have the meanings indicated above and X is O (oxygen) or N-Prot, by elimination (dehydration) in a manner known per se, preferably with acidic catalysis and/or using a suitable dehydrating agent (see, for example, Patai-Rappaport, The Chemistry of the Hydroxyl Group, Vol. 2, pp. 641–718, New York, Wiley 1971). The preparation of the compounds of the formula 5 is described by way of example in the examples.

The following examples serve to explain the invention in greater detail without restricting it. Likewise, further compounds of the formula 1, whose preparation is not described explicitly, can be prepared in an analogous manner or in a manner familiar per se to the person skilled in the art using customary process techniques. The abbreviation min stands for minute(s), h for hour(s) and m.p. for melting point.

EXAMPLES
Final Products of the Formula 1

1. (7S,8R,9R)-10-Acetyl-7,8-epoxy-2,3-dimethyl-7,8,9,10-tetrahydroimidazo[1,2-h][1,7]naphthyridine 98.0 g of (7R,8R,9R)-10-acetyl-7,8-dihydroxy-2,3-dimethyl-9-phenyl-7,8,9,10-tetra hydroimidazo[1,2-h]-[1,7]naphthyridine are suspended in 720 ml of dichloromethane under nitrogen, with exclusion of moisture and ice cooling. After addition of 79 ml of tributylphosphine, 60 ml of diisopropyl azodicarboxylate are added dropwise at an internal temperature of 5° C. over the course of 45 min. After addition is complete, the orange-colored solution is stirred for a further 20 min with ice cooling. The reaction mixture is added to 1 l of ice water, the organic phase is separated off and the aqueous phase is extracted with dichloromethane (2×100 ml). The combined organic phases are washed with water (3×500 ml) and dried over sodium sulfate. On concentrating the organic phase on a rotary evaporator (bath temp. <40° C.) to about 1/10 of the volume, the crystalilzation of the product begins. 500 ml of tert-butyl methyl ether are then slowly added dropwise with stirring. After stirring for 1 h with ice cooling, the precipitate is filtered off with suction and washed with 200 ml of tert-butyl methyl ether. The product is dried to constant weight at 40° C. in a vacuum drying oven. 86.0 g (92%) of the title compound are isolated as a colorless solid of m.p. 205–206° C.

2. rel-(7S,8R,9R)-10-Acetyl-7,8-epoxy-2,3-dimethyl-9-phenyl-7,8,9,10-tetrahydroimidazo[1,2-h]-[1,7]naphthyridine (Racemic)

0.64 g (2 mmol) of rac-10-acetyl-2,3-dimethyl-9-phenyl-9,10-dihydroimidazo[1,2-h][1,7]naphthyridine (racemic) are dissolved in 3 ml of acetonitrile and 1 ml of methanol and treated with 0.18 g (1.2 mmol) of potassium carbonate. 0.2 ml of hydrogen peroxide solution (30% in water) is then slowly added dropwise with ice cooling. The mixture is then allowed to warm to room temperature and is stirred for 16 h. After addition of saturated sodium hydrogencarbonate solution, it is extracted with dichloromethane. The organic phase is dried over magnesium sulfate and evaporated. The residue is purified by chromatography on silica gel (eluent diethyl ether/triethylamine 9:1). After crystallization from diethyl ether, 80 mg (12%) of the title compound are isolated as a colorless solid (m.p. 222° C.).

Starting Compounds of the Formula 2

A. (8R,9R)-2,3-Dimethyl-9-phenyl-8-pivaloyloxy-7,8,9,10-tetrahydroimidazo[1,2-h][1,7]naphthyridin-7-one 140 g of (8R,9R)-2,3-dimethyl-8-hydroxy-9-phenyl-7,8,9,10-tetrahydroimidazo[1,2-h][1,7]naphthyridin-7-one (WO 00/17200, example B1) are suspended in 1100 ml of dichloromethane under argon and with exclusion of moisture. After addition of 70 ml of triethylamine and 2.5 g of 4-dimethyl-aminopyridine, a solution of 62 ml of pivaloyl chloride in 70 ml of dichloromethane is added dropwise such that the temperature of the reaction mixture does not rise above 30° C. (cooling with a water bath). After stirring overnight, the mixture is added to 1 l of ice water and stirred in the cold for a further 10 min. The organic phase is separated off and the aqueous phase is extracted with dichloromethane (2×200 ml). The combined organic phases are washed with water (3×300 ml) until neutral, dried over sodium sulfate and evaporated. 220 g of yellowish oil are obtained, which is crystallized using 600 ml of tert-butyl methyl ether. After stirring in the cold for 2 h, the solid is filtered off, washed with 200 ml of tert-butyl methyl ether and the filter residue is dried to constant weight in a vacuum drying oven. 175 g (97%) of the title compound are obtained as a slightly yellowish solid of m.p. 185–187° C.

B. (8R,9R)-10-Acetyl-2,3-dimethyl-9-phenyl-8-pivaloyloxy-7,8,9,10-tetrahydroimidazo[1,2-h]-[1,7]naphthyridin-7-one 175 g of (8R,9R)-2,3-dimethyl-9-phenyl-8-pivaloyloxy-7,8,9,10-tetrahydroimidazo[1,2-h][1,7]naphthyridin-7-one are dissolved in 2200 ml of toluene under argon and with exclusion of moisture with mechanical stirring. Half the amount of acetyl chloride (130 ml in total) is then added dropwise with ice cooling in the course of 30 min. After removing the ice bath, half the amount of triethylamine (250 ml in total) is then added dropwise at 10° C. in the course of 40 min (warming to 30° C.). After 15 min at this temperature, the procedure is repeated as described with the second half of the reagents indicated. The mixture is then added to 1 l of ice water with stirring. The organic phase is separated off and the aqueous phase is extracted with ethyl acetate (2×200 ml). The combined organic phases are washed with water (3×400 ml), dried over sodium sulfate and evaporated. The yellow-brown residue is crystallized using 300 ml of tert-butyl methyl ether. After stirring in the cold for 1 h, it is filtered off, washed with 200 ml of tert-butyl methyl ether and the filter residue is dried to constant weight in a vacuum drying oven. 186 g (95%) of the title compound are isolated as a yellowish solid of m.p. 168–170° C.

C. (7R,8R,9R)-10-Acetyl-7-hydroxy-2,3-dimethyl-9-phenyl-8-pivaloyloxy-7,8,9,10-tetrahydroimidazo[1,2-h][1,7]naphthyridine 165 g of (8R,9R)-10-acetyl-2,3-dimethyl-9-phenyl-8-pivaloyloxy-7,8,9,10-tetrahydroimidazo[1,2-h]-[1,7]

naphthyridin-7-one are suspended in 2.0 l of isopropanol with mechanical stirring. 47.8 g of sodium cyanoborohydride are then introduced with ice cooling. After addition of 20 drops of Methyl Orange, methanolic hydrogen chloride solution is slowly added dropwise until the color change to red persists (approximately 150 ml, 1 h, warming of the reaction mixture to 16° C.). After a further 20 min, the mixture is added to 1.5 l of ice water and 1 l of dichloromethane and neutralized with ammonia solution (25%). The organic phase is separated off and the aqueous phase is extracted with 250 ml of dichloromethane. The combined organic phases are reextracted with water (3×1.5 l), dried over sodium sulfate and evaporated on a rotary evaporator. Coevaporation with acetone (3×) and drying of the residue in a high vacuum yields 160 g (90%) of the title compound as a colorless foam of m.p. 103–105° C., which is used without further purification in the next stage.

D. (7R,8R,9R)-10-Acetyl-7,8-dihydroxy-2,3-dimethyl-9-phenyl-7,8,9,10-tetrahydroimidazo[1,2-h][1,7]naphthyridine 160 g of (7R,8R,9R)-10-acetyl-7-hydroxy-2,3-dimethyl-9-phenyl-8-pivaloyloxy-7,8,9,10-tetrahydroimidazo[1,2-h][1,7]naphthyridine are dissolved in 0.7 l of methanol with stirring and treated with 40 g of potassium carbonate. After approximately 10 min, the product begins to precipitate from the reaction mixture. After stirring for 1 h at room temperature, it is added to a solution of 200 g of ammonium chloride in 1.8 l of ice water. It is stirred for a further 1 h at ice-bath temperature, then the precipitated solid is filtered off with suction and washed with a little methanol (80 ml). After drying at 50° C. in a vacuum drying oven, 92.0 g (73%) of the title compound are isolated as a colorless solid of m.p. 260–261° C., which is used in the next stage without further purification. Alternatively, the tile compound can also be prepared according to examples 5 and 6.

E. (8R,9R)-8,10-Diacetyl-2,3-dimethyl-9-phenyl-7,8,9,10-tetrahydroimidazo[1,2-h][1,7]naphthyridin-7-one 50 g of (8R,9R)-2,3-dimethyl-8-hydroxy-9-phenyl-7,8,9,10-tetrahydroimidazo[1,2-h][1,7]naphthyridin-7-one (WO 00/17200, example B1) are dissolved under nitrogen and with exclusion of moisture in 450 ml of dichloromethane. Half of the amount of acetyl chloride (46.6 ml in total) is firstly added dropwise at room temperature. Half the amount of triethylamine (45 ml in total) is then added dropwise with ice cooling in the course of 30 min. After stirring at room temperature for 1 h, the procedure is repeated as described with the second half of the reagents indicated. The mixture is then hydrolyzed using saturated sodium hydrogencarbonate solution and water. The organic phase is separated off and the aqueous phase is extracted with dichloromethane. The combined organic phases are dried over magnesium sulfate and evaporated. The yellow-brown residue is coevaporated a further two times with toluene. 64 g of the title compound are isolated as a brown oil, which is used in the next stage without further purification.

F. (7R,8R,9R)-10-Acetyl-7,8-dihydroxy-2,3-dimethyl-9-phenyl-7,8,9,10-tetrahydroimidazo[1,2-h]-[1,7]naphthyridine 64 g of (8R,9R)-8,10-diacetyl-2,3-dimethyl-9-phenyl-7,8,9,10-tetrahydroimidazo[1,2-h][1,7]naphthyridin-7-one (crude product) are dissolved in 250 ml of methanol. 12.3 g of sodium borohydride are introduced with ice cooling. After stirring for 1 h, 23 g of potassium carbonate are added to the reaction mixture and it is stirred for a further 2 h at room temperature. It is then added to ice water and the precipitate is filtered off with suction. After washing the precipitate with acetone and ether, 37 g of the title compound are isolated.

Starting Compounds of the Formula 3

I. (9S)-2,3-Dimethyl-9-phenyl-5,6,7,8,9,10-hexahydroimidazo[1,2-h][1,7]naphthyridin-7-one 9.7 g (51.6 mmol) of ethyl (S)-3-amino-3-phenylpropionate, 8.5 g (51.6 mmol) of 2,3-dimethyl-6,7-dihydro-5H-imidazo[1,2-a]pyridin-8-one and 0.26 g (1.3 mmol) of p-toluenesulfonic acid monohydrate are heated under reflux in 50 ml of toluene in a water separator. After water no longer separates, the reaction mixture is cooled to 0° C. and diluted with 100 ml of tetrahydrofuran. 7.24 g (64.5 mmol) of potassium tert-butoxide are then introduced and the mixture is stirred at room temperature for 16 h. 150 ml of saturated ammonium chloride solution are added to the reaction mixture, the organic phase is separated off and the aqueous phase is extracted with 300 ml of ethyl acetate. The combined organic phases are washed with 250 ml of water, dried over sodium sulfate and evaporated. 13.27 g (88%) of the title compound are isolated as a red-brown oil. An analytical sample is obtained by crystallization using diethyl ether (red solid, m.p. 134° C.).

II. (9S)-2,3-Dimethyl-9-phenyl-7,8,9,10-tetrahydroimidazo[1,2-h][1,7]naphthyridin-7-one 63.5 g (0.22 mol) of (9S)-2,3-dimethyl-9-phenyl-5,6,7,8,9,10-hexahydroimidazo[1,2-h][1,7]naphthyridin-7-one are dissolved in 250 ml of toluene and 250 ml of tetrahydrofuran and cooled to 0° C. 59 g (0.26 mol) of 2,3-dichloro-5,6-dicyano-1,4-benzoquinone are introduced in portions of 10 g over a period of 1 h with mechanical stirring. The reaction mixture is stirred at room temperature for 16 h. 1.2 l of 0.5 N sodium hydroxide solution and 1 l of ethyl acetate are then added dropwise. The organic phase is separated off and washed with water. The aqueous phase is reextracted with ethyl acetate and the combined organic phases are dried over sodium sulfate and evaporated. The residue is crystallized in 300 ml of methanol at 0° C. The solid is filtered off with suction, washed with cold methanol and dried. 20 g (32%) of the title compound are isolated as a slightly yellow solid (m.p. 103–105° C.).

III. rac-7-Acetoxy-10-acetyl-2,3-dimethyl-9-phenyl-9,10-dihydroimidazo[1,2-h][1,7]naphthyridine 90 g (0.31 mol) of rac-2,3-dimethyl-9-phenyl-7,8,9,10-tetrahydroimidazo[1,2-h][1.7]naphthyridin-7-one are suspended in 250 ml of acetic anhydride and treated with 20 ml of methanesulfonic acid. The mixture is then heated under reflux for 3 h. After cooling, the acetic anhydride is distilled off in vacuo and the oily residue is added to 200 ml of water. The pH of the mixture is brought to pH 9 by addition of concentrated ammonia solution with stirring. After addition of 200 ml of water, it is extracted with methylene chloride. The organic phase is washed with water, dried over magnesium sulfate and evaporated. The residue is crystallized using diethyl ether, and the precipitate is filtered off with suction and washed with diethyl ether. 85.4 g (74%) of the title compound are isolated as a yellow solid (m.p. 237–239° C.).

IV. (9S)-7-Acetoxy-10-acetyl-2,3-dimethyl-9-phenyl-9,10-dihydroimidazo[1,2-h][1,7]naphthyridine 8.7 g (0.03 mol) of (9S)-2,3-dimethyl-9-phenyl-7,8,9,10-tetrahydroimidazo[1,2-h][1,7]naphthyridin-7-one are suspended in 49 ml of acetic anhydride, treated with 2 ml of methanesulfonic acid and heated under reflux. After 30 min, 2 ml of methanesulfonic acid are again added. After 1 h, the reaction mixture is added to 250 ml of ice water and neutralized by addition of concentrated ammonia solution. It is extracted with methylene chloride, and the organic phase is dried over magnesium sulfate and evaporated. The residue is crystallized using diethyl ether, and the precipitate is filtered off with suction and washed with diethyl ether. 7.2 g (65%) of the title compound are isolated as a yellow solid (m.p. 237–239° C.).

V. rel-(7S,9S)-10-Acetyl-7-hydroxy-2,3-dimethyl-9-phenyl-7,8,9,10-tetrahydroimidazo[1,2h][1,7]naphthyridine (Racemic)

12.2 g (32.5 mmol) of rac-7-acetoxy-10-acetyl-2,3-dimethyl-9-phenyl-9,10-dihydroimidazo[1,2-h][1,7]naphthyridine are dissolved in 50 ml of methanol and 10 ml of dichloromethane. 5.0 g (132 mmol) of sodium borohydride are then introduced at 0° C. over a period of 2 h. After 3 h, 30 ml of saturated ammonium chloride solution are added. The reaction mixture is extracted with dichloromethane, and the organic phase is dried over magnesium sulfate and evaporated. The residue is crystallized using diethyl ether. 8.2 g (75%) of the title compound are isolated as a colorless solid (m.p. 217° C.).

VI. rac-10-Acetyl-2,3-dimethyl-9-phenyl-9,10-dihydroimidazo[1,2-h][1,7]naphthyridine (Racemic)

6.0 g (17.9 mmol) of rel-(7S,9S)-10-acetyl-7-hydroxy-2,3-dimethyl-9-phenyl-7,8,9,10-tetrahydroimidazo[1,2-h][1,7]naphthyridine (racemic) are dissolved in 100 ml of dichloromethane and 20 ml of triethylamine. A solution of 2.9 g (25 mmol) of methanesulfonyl chloride in 5 ml of dichloromethane is then added dropwise with ice cooling in the course of 30 min. After 2 h, the mixture is hydrolyzed with water and extracted with dichloromethane. The organic phase is dried over magnesium sulfate and evaporated. The residue is crystallized using diethyl ether. 4.8 g (85%) of the title compound are isolated as a slightly brown solid (m.p. 170° C.).

Use of Compounds of the Formula 1 According to the Invention for the Preparation of Active Compounds of the Formula 4 a) (7R,8R,9R)-10-Acetyl-8-hydroxy-7-(2-methoxyethoxy)-2,3-dimethyl-9-phenyl-7,8,9,10-tetrahydroimidazo[1,2-h][1,7]naphthyridine 85.0 g of (7S,8R,9R)-10-acetyl-7,8-epoxy-2,3-dimethyl-7,8,9,10-tetrahydroimidazo[1,2-h][1,7]naphthyridine are suspended in 800 ml of 2-methoxyethanol with stirring. After cooling the reaction mixture to 5° C. by means of an ice bath, 1.6 ml of phosphoric acid are added dropwise. After stirring for 15 h, a further 1.6 ml of phosphoric acid are added and the mixture is allowed to stand at 0° C. for 2 days. It is then added to a mixture of 1 l of ice water and 1 l of dichloromethane and neutralized with saturated sodium carbonate solution. The organic phase is separated off and the aqueous phase is extracted with dichloromethane (3×300 ml). The combined organic phases are washed with water (3×500 ml), dried over sodium sulfate and evaporated on a rotary evaporator. The residue is coevaporated with acetone a further three times and dried in a high vacuum. 94.0 g (90%) of the title compound are obtained as a colorless foam (diastereomer ratio 95:5, HPLC). The crude product is employed in the next stage without further purification.

b) (7R,8R,9R)-8-Hydroxy-7-(2-methoxyethoxy)-2,3-dimethyl-9-phenyl-7,8,9,10-tetrahydroimidazo[1,2-h][1,7]naphthyridine 94.0 g of (7R,8R,9R)-10-acetyl-8-hydroxy-7-(2-methoxyethoxy)-2,3-dimethyl-9-phenyl-7,8,9,10-tetrahydroimidazo[1,2-h][1,7]naphthyridine are suspended in 500 ml of 2-aminoethanol with stirring and treated with 6.0 g of potassium carbonate. The reaction mixture is heated to 90° C. for 1 h. It is then cooled using an ice bath and added to a mixture of 1.5 l of ice water and 700 ml of dichloromethane. The organic phase is separated off and the aqueous phase is extracted with dichloromethane (4×300 ml). The combined organic phases are washed with water (4×500 ml) and saturated ammonium chloride solution, dried over sodium sulfate and evaporated on a rotary evaporator. The residue is coevaporated with acetone a further three times and dried in a high vacuum. 88.0 g of crude product are obtained, which is dissolved in 300 ml of acetone and treated with a solution of 27.0 g of maleic acid in 100 ml of acetone with stirring. After allowing to stand overnight in a refrigerator, the precipitated solid is filtered off with suction, washed with 120 ml of cold acetone and dried to constant weight in a vacuum drying oven. 88.0 g of the maleate of the title compound are obtained as a colorless solid. 85.0 g of this are suspended in 350 ml of acetone and 350 ml of water with mechanical stirring. A solution of 14.0 g of sodium hydroxide in 20 ml of water is then added dropwise, then a further 500 ml of water, and the suspension is stirred at ice-bath temperature for 1 h. The precipitate is filtered off with suction, washed with water and acetone until neutral and dried at 50° C. in a vacuum drying oven. 64.0 g of colorless solid are obtained, which is precipitated with stirring from 180 ml of ethyl acetate at 60° C. After drying in a vacuum drying oven, 57.5 g (68%) of the title compound are isolated as a colorless solid of m.p. 129–131° C.

Commercial Utility

The compounds of the formula 1 and their salts are valuable intermediates for the preparation of active compounds, such as are disclosed, for example, in the international patent applications WO 98/42707, WO 98/54188, WO 00/17200, WO 00/26217 and WO 00/63211, and of compounds of the formula 2 structurally related thereto.

What is claimed is:
1. A compound of the formula 1

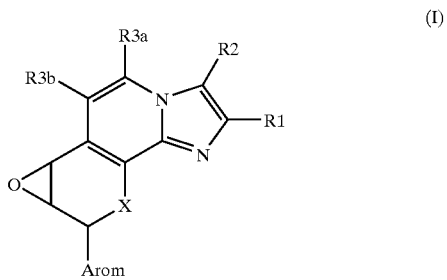

in which
R1 is hydrogen, 1–4C-alkyl, 3–7C-cycloalkyl, 3–7C-cycloalkyl-1–4C-alkyl, 1–4C-alkoxy, 1–4C-alkoxy-1–4C-alkyl, 1–4C-alkoxycarbonyl, 2–4C-alkenyl, 2–4C-alkynyl, fluoro-1–4C-alkyl or hydroxy-1–4C-alkyl,
R2 is hydrogen, 1–4C-alkyl, 3–7C-cycloalkyl, 3–7C-cycloalkyl-1–4C-alkyl, 1–4C-alkoxycarbonyl, hydroxy-1–4C-alkyl, halogen, 2–4C-alkenyl, 2–4C-alkynyl, fluoro-1–4C-alkyl or cyanomethyl, R3a is hydrogen, halogen, fluoro-1–4C-alkyl, 1–4C-alkyl, 2–4C-alkenyl, 2–4C-alkynyl, 1–4C-alkoxy, carboxyl, 1–4C-alkoxycarbonyl, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32, R3b is hydrogen, halogen, fluoro-1–4C-alkyl, 1–4C-alkyl, 2–4C-alkenyl, 2–4C-alkynyl, 1–4C-alkoxy, carboxyl, 1–4C-alkoxycarbonyl, hydroxy-1–4C-alkyl, 1–4C-alkoxy-1–4C-alkyl, 1–4C-alkoxy-1–4C-alkoxy-1–4C-alkyl, fluoro-1–4C-alkoxy-1–4C-alkyl or the radical —CO—NR31R32, where R31 is hydrogen, 1–7C-alkyl, hydroxy-1–4C-alkyl or 1–4C-alkoxy-1–4C-alkyl and R32 is hydrogen, 1–7C-alkyl, hydroxy-1–4C-alkyl or 1–4C-alkoxy-1–4C-alkyl, or where R31 and R32 together, including the nitrogen atom to which both are bonded, are a pyrrolidino radical, piperidino radical or morpholino radical, Arom is a mono- or bicyclic aromatic radical substituted by R4, R5, R6 and R7, which is selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuryl), thiophenyl (thienyl), benzothiophenyl (benzothienyl), thiazolyl, isoxazolyl, pyridinyl, pyrimidinyl, quinolinyl and isoquinolinyl, where R4 is hydrogen, 1–4C-alkyl, hydroxy-1–4C-alkyl, 1–4C-alkoxy, 2–4C-alkenyloxy, 1–4C-alkylcarbonyl, carboxyl, 1–4C-alkoxycarbonyl, carboxy-1–4C-alkyl, 1–4C-alkoxycarbonyl-1–4C-alkyl, halogen, hydroxyl, aryl, aryl-1–4C-alkyl, aryloxy, aryl-1–4C-alkoxy, trifluoromethyl, nitro, amino, mono- or di-1–4C-alkylamino, 1–4C-alkylcarbonylamino, 1–4C-alkoxycarbonylamino, 1–4C-alkoxy-1–4C-alkoxycarbonylamino or sulfonyl, R5 is hydrogen, 1–4C-alkyl, 1–4C-alkoxy, 1–4C-alkoxycarbonyl, halogen, trifluoromethyl or hydroxyl, R6 is hydrogen, 1–4C-alkyl or halogen and R7 is hydrogen, 1–4C-alkyl or halogen, where aryl is phenyl or substituted phenyl having one, two or three identical or different substituents selected from the group consisting of 1–4C-alkyl, 1–4C-alkoxy, carboxyl, 1–4C-alkoxycarbonyl, halogen, trifluoromethyl, nitro, trifluoromethoxy, hydroxyl and cyano, X is O (oxygen), NH or N-Prot, where Prot is an amino protective group, or a hydrate, solvate, salt, hydrate of a salt or solvate of a salt thereof.

2. A compound of the formula I as claimed in claim 1, in which

R1 is hydrogen, 1–4C-alkyl, 3–7C-cycloalkyl, 1–4C-alkoxy-1–4C-alkyl, 2–4C-alkynyl or fluoro-1–4C-alkyl, R2 is hydrogen, 1–4C-alkyl, halogen, 2–4C-alkenyl, 2–4C-alkynyl or fluoro-1–4C-alkyl, R3a is hydrogen, R3b is hydrogen, halogen, 1–4C-alkyl or the radical —CO—NR31R32, where R31 is hydrogen, 1–7C-alkyl, hydroxy-1–4C-alkyl or 1–4C-alkoxy-1–4C-alkyl and R32 is hydrogen, 1–7C-alkyl, hydroxy-1–4C-alkyl or 1–4C-alkoxy-1–4C-alkyl, or where R31 and R32 together, including the nitrogen atom to which both are bonded, are a pyrrolidino radical, piperidino radical or morpholino radical, Arom is a mono- or bicyclic aromatic radical substituted by R4, R5, R6 and R7, which is selected from the group consisting of phenyl, furanyl (furyl) and thiophenyl (thienyl), where R4 is hydrogen, 1–4C-alkyl, hydroxy-1–4C-alkyl, 1–4C-alkoxy, 1–4C-alkylcarbonyl, carboxyl, 1–4C-alkoxycarbonyl, halogen, hydroxyl, trifluoromethyl, 1–4C-alkylcarbonylamino, 1–4C-alkoxycarbonylamino, 1–4C-alkoxy-1–4C-alkoxycarbonylamino or sulfonyl, R5 is hydrogen, 1–4C-alkyl, 1–4C-alkoxy, 1–4C-alkoxycarbonyl, halogen, trifluoromethyl or hydroxyl, R6 is hydrogen and R7 is hydrogen, X is O (oxygen), NH or N-Prot, where Prot is an amino protective group, or a hydrate, solvate, salt, hydrate of a salt or solvate of a salt thereof.

3. A compound as claimed in claim 1, represented by the formula 1*,

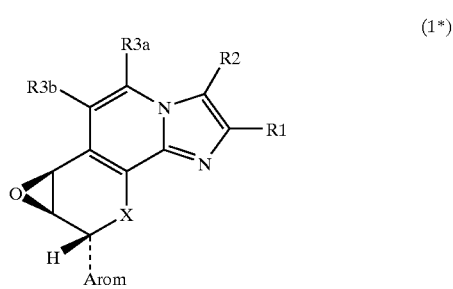

(1*)

in which

R1 is hydrogen, methyl, cyclopropyl, methoxymethyl or trifluoromethyl,

R2 is hydrogen, methyl, chloro, bromo, ethynyl or trifluoromethyl,

R3a is hydrogen,

R3b is hydrogen, fluoro, methyl or the radical —CO—N(CH$_3$)$_2$,

Arom is a phenyl radical and

X is O (oxygen), NH or N-Prot, where Prot is an amino protective group, or a hydrate, solvate, salt, hydrate of a salt or solvate of a salt thereof.

4. A compound as claimed in claim 1, represented by the formula 1*

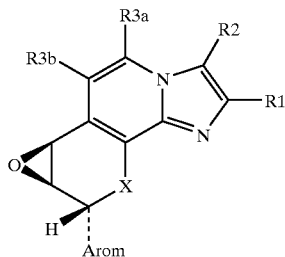

(1*)

in which

R1 is methyl,
R2 is methyl,
R3a is hydrogen,
R3b is hydrogen,
Arom is a phenyl radical and
X is O (oxygen), NH or N-Prot,
where Prot is an amino protective group,
or a hydrate, solvate, salt, hydrate of a salt or solvate of a salt thereof.

5. A process for preparing a compound of the formula 4

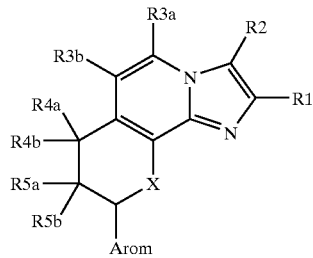

(4)

in which R1, R2, R3a, R3b and Arom have the meanings indicated in claim 1 and X is O (oxygen), NH or N-Prot,
one of the substituents R4a and R4b is hydrogen and the other is 1–4C-alkoxy, 1–4C-alkoxy which is substituted by oxo, 3–7C-cycloalkoxy, 3–7C-cycloalkyl-1–4C-alkoxy, 1–4C-alkoxy-1–4C-alkoxy, 3–7C-cycloalkoxy-1–4C-alkoxy, 3–7C-cycloalkyl-1–4C-alkoxy-1–4C-alkoxy or 1–4C-alkoxy which is substituted by halogen,
one of the substituents R5a and R5b is hydrogen and the other is hydroxyl,
or a hydrate, solvate, salt, hydrate of a salt or solvate of a salt thereof,
comprising reacting a compound of formula I as claimed in claim 1, in which R1, R2, R3a, R3b and Arom have the meanings indicated in claim 1 and X is O (oxygen) or N-Prot, where Prot is an amino protective group,
with one or more alcohols of the formula ROH,
in which
RO is 1–4C-alkoxy, 1–4C-alkoxy which is substituted by oxo, 3–7C-cycloalkoxy, 3–7C-cycloalky-1–4C-alkoxy, 1–4C-alkoxy-1–4C-alkoxy, 3–7C-cycloalkoxy-1–4C-alkoxy, 3–7C-cycloalkyl-1–4C-alkoxy-1–4C-alkoxy or 1–4C-alkoxy which is substituted by halogen.

6. A process for preparing a compound of the formula 4*

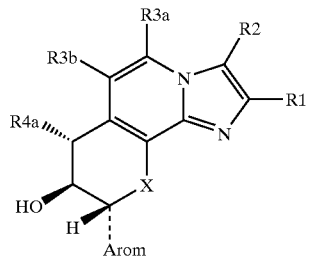

(4*)

in which R1, R2, R3a, R3b and Arom have the meanings indicated in claim 3 and X is O (oxygen), NH or N-Prot,
R4a is 1–4C-alkoxy, 1–4C-alkoxy which is substituted by oxo, 3–7C-cycloalkoxy, 3–7C-cycloalkyl-1–4C-alkoxy, 1–4C-alkoxy-1–4C-alkoxy, 3–7C-cycloalkoxy-1–4C-alkoxy, 3–7C-cycloalkyl-1–4C-alkoxy-1–4C-alkoxy or 1–4C-alkoxy which is substituted by halogen,
or a hydrate, solvate, salt, hydrate of a salt or solvate of a salt thereof,
comprising reacting a compound of formula 1* as claimed in claim 3, in which R1, R2, R3a, R3b and Arom have the meanings indicated in claim 3 and X is O (oxygen) or N-Prot, where Prot is an amino protective group,
with one or more alcohols of the formula ROH,
in which
RO is 1–4C-alkoxy, 1–4C-alkoxy which is substituted by oxo, 3–7C-cycloalkoxy, 3–7C-cycloalkyl-1 –4C-alkoxy, 1–4C-alkoxy-1–4C-alkoxy, 3–7C-cycloalkoxy-1–4C-alkoxy, 3–7C-cycloalkyl-1–4C-alkoxyl-1–4C-alkoxy or 1–4C-alkoxy which is substituted by halogen.

7. A process for preparing a compound of the formula 4* as in claim 6, in which
R1 is methyl,
R2 is methyl,
R3a is hydrogen,
R3b is hydrogen,
R4a is methoxy, ethoxy or methoxyethoxy,
Arom is a phenyl radical and
X is O (oxygen) NH or N-Prot,
or a hydrate, solvate, salt, hydrate of a salt or solvate of a salt thereof,
comprising reacting a compound of formula 1*

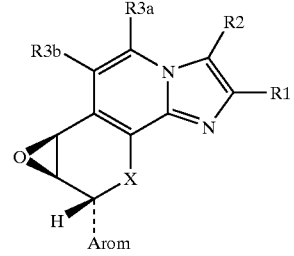

(1*)

in which
R1 is methyl,
R2 is methyl,
R3a is hydrogen,
R3b is hydrogen,
Arom is a phenyl radical and X is O (oxygen) or N-Prot, where Prot is an amino protective group,
with one or more alcohols of the formula ROH,
in which
RO is 1–4C-alkoxy, 1–4C-alkoxy which is substituted by oxo, 3–7C-cycloalkoxy, 3–7C-cycloalkyl-1–4C-alkoxy, 1–4C-alkoxy-1–4C-alkoxy, 3–7C-cycloalkoxy-1–4C-alkoxy, 3–7C-cycloalkyl-1–4C-alkoxy-1–4C-alkoxy or 1–4C-alkoxy which is substituted by halogen.

8. A process for preparing a compound of the formula 4* as in claim 6, in which
R1 is methyl,
R2 is methyl,
R3a is hydrogen,
R3b is hydrogen,
R4a is methoxy, ethoxy or methoxyethoxy,
Arom is a phenyl radical and
X is NH or N-Prot,
or a hydrate, solvate, salt, hydrate of a salt or solvate of a salt thereof,
comprising reacting a compound of formula 1*

(1*)

in which
R1 is methyl,
R2 is methyl,
R3a is hydrogen,
R3b is hydrogen,
Arom is a phenyl radical and X is N-Prot, where Prot is an amino protective group,
with one or more alcohols of the formula ROH,
in which
RO is 1–4C-alkoxy, 1–4C-alkoxy which is substituted by oxo, 3–7C-cycloalkoxy, 3–7C-cycloalkyl-1–4C-alkoxy, 1–4C-alkoxy-1–4C-alkoxy, 3–7C-cycloalkoxy-1–4-alkoxy, 3–7C-cycloalkyl-1–4C-alkoxy-1–4C-alkoxy or 1–4C-alkoxy which is substituted by halogen.

9. A process for preparing a compound of the formula 4* as in claim 6, in which
R1 is methyl,
R2 is methyl,
R3a is hydrogen,
R3b is hydrogen,
R4a is methoxy, ethoxy or 2-methoxyethoxy,
Arom is a phenyl radical and
X is NH or N-Prot,
or a hydrate, solvate, salt, hydrate of a salt or solvate of a salt thereof,
which comprises reacting a compound of the formula 1*

(1*)

in which
R1 is methyl,
R2 is methyl,
R3a is hydrogen,
R3b is hydrogen,
Arom is a phenyl radical and
X is N-Prot,
where Prot is an amino protective group,
with methanol, ethanol or 2-methoxyethanol.

10. The process according to claim 9, further comprising the step of removing the amino protective group.

* * * * *

UNITED STATES PATENT AND TRADEMARK OFFICE
CERTIFICATE OF CORRECTION

PATENT NO.         : 6,927,292 B2                                    Page 1 of 1
APPLICATION NO.    : 10/485418
DATED              : August 9, 2005
INVENTOR(S)        : Senn-Bilfinger et al.

It is certified that error appears in the above-identified patent and that said Letters Patent is hereby corrected as shown below:

Claim 5, Column 23, Line 64, Please delete
"3-7C-cycloalky-1-4C-alkoxy,"
and replace with
-- 3-7C-cycloalkyl-1-4C-alkoxy, --

Claim 6, Column 24, Lines 35-36, Please delete
"3-7C-cycloalkyl-1  -4C-alkoxy," and replace with
-- 3-7C-cycloalkyl-1-4C-alkoxy, --

Claim 6, Column 24, Lines 37-38, Please delete
"3-7C-cycloalkyl-1-4C-alkoxyl-1-4C-alkoxy,"
and replace with
-- 3-7C-cycloalkyl-1-4C-alkoxy-1-4C-alkoxy, --

Claim 8, Column 26, Lines 4-5, Please delete
"3-7C-cycloalkyl-1-4-alkoxy," and replace with
-- 3-7C-cycloalkyl-1-4C-alkoxy, --

Signed and Sealed this

Nineteenth Day of December, 2006

JON W. DUDAS
*Director of the United States Patent and Trademark Office*